(12) United States Patent
McPhee

(10) Patent No.: US 6,371,937 B1
(45) Date of Patent: Apr. 16, 2002

(54) MANOMETER INFUSION APPARATUS

(75) Inventor: Charles J. McPhee, Huntington Beach, CA (US)

(73) Assignee: I-Flow Corporation, Lake Forest, CA (US)

( * ) Notice: Subject to any disclaimer, the term of this patent is extended or adjusted under 35 U.S.C. 154(b) by 0 days.

(21) Appl. No.: 09/535,860

(22) Filed: Mar. 27, 2000

(51) Int. Cl.⁷ ............................................. A61M 1/00
(52) U.S. Cl. ................... 604/118; 604/48; 604/93.01; 73/714
(58) Field of Search .................. 73/708, 714; 604/118, 604/93.01, 48; 600/485–488

(56) References Cited

U.S. PATENT DOCUMENTS

| | | |
|---|---|---|
| 387,663 A | 8/1888 | Sutley |
| 394,974 A | 12/1888 | Guss et al. |
| 438,597 A | 10/1890 | Ashton |
| 2,600,324 A | 6/1952 | Rappaport |
| 2,625,153 A | 1/1953 | Baum |
| 2,866,453 A | 12/1958 | Jewett |
| 3,233,457 A | 2/1966 | Martinez |
| 3,242,920 A | 3/1966 | Andersen |
| 3,435,819 A | 4/1969 | Reynolds et al. |
| 3,460,526 A | 8/1969 | McKirdy et al. |
| 3,590,818 A | 7/1971 | Lemole |
| 3,610,230 A | 10/1971 | Andersen |
| 3,690,318 A | 9/1972 | Gorsuch |
| 3,730,168 A | 5/1973 | McWhorter |
| 3,807,389 A | 4/1974 | Miller et al. |
| 3,850,348 A | 11/1974 | Bessot et al. |
| 3,920,002 A | 11/1975 | Dye et al. |
| 3,934,576 A | 1/1976 | Danielsson |
| 3,980,082 A | 9/1976 | Miller |
| 4,043,332 A | 8/1977 | Metcalf |
| 4,135,509 A | 1/1979 | Shannon |
| 4,157,718 A | 6/1979 | Baehr |
| 4,184,491 A | 1/1980 | McGannon |
| 4,217,911 A | 8/1980 | Layton |
| 4,282,881 A | 8/1981 | Todd et al. |
| 4,785,821 A | 11/1988 | Udell et al. |
| 5,098,304 A | 3/1992 | Abrams |
| 5,454,374 A | * 10/1995 | Omachi ...................... 600/486 |

FOREIGN PATENT DOCUMENTS

| | | |
|---|---|---|
| WO | WO 82/02657 | 1/1982 |

* cited by examiner

*Primary Examiner*—Eric F. Winakur
*Assistant Examiner*—Ryan Carter
(74) *Attorney, Agent, or Firm*—Knobbe, Martens, Olson & Bear, LLP

(57) ABSTRACT

A manometer for measuring the hydrodynamic pressure of fluids parenterally administered to a patient is disclosed. The manometer includes a transparent housing that has a passage that accommodates continuous flow of fluid. A pressure-measuring chamber is formed in the housing with one end in fluid communication with the passage. The other end of the chamber communicates with an enclosed air space. The fluid flowing through the passage enters the pressure-measuring chamber and rises to a level which is dependent upon the pressure of the fluid flowing through the passage. A space-saving chamber is provided, which is in air communication with the pressure-measuring chamber, and which allows the housing to be reduced in size. Markings are provided on the housing which indicate the relative flow state of fluid flowing through the passage.

13 Claims, 4 Drawing Sheets

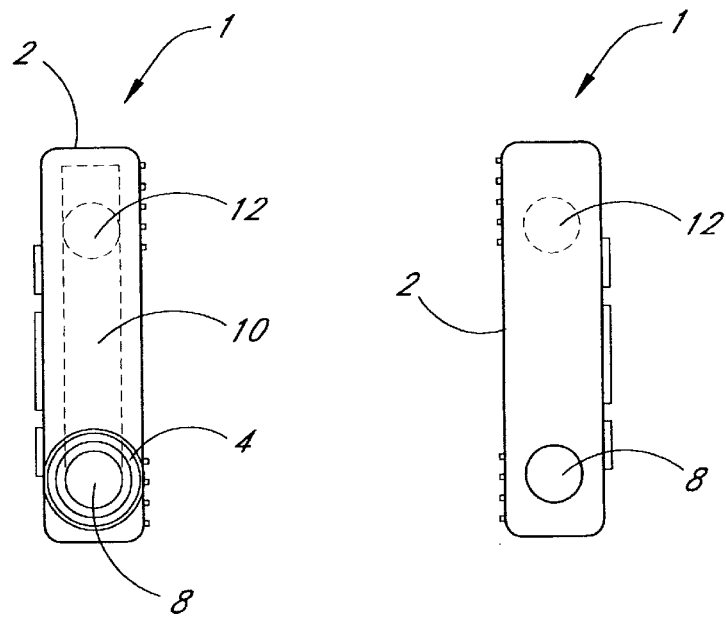
FIG. 4  FIG. 5
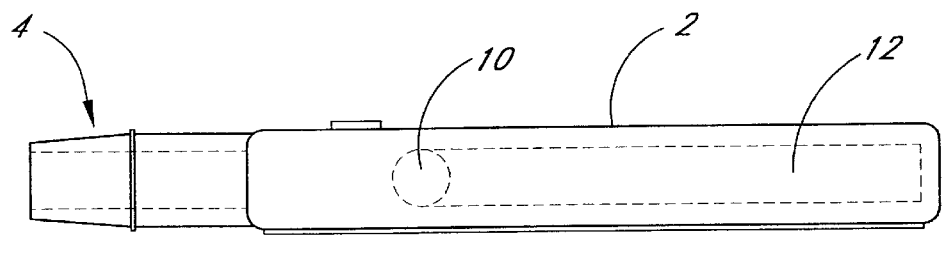
FIG. 6
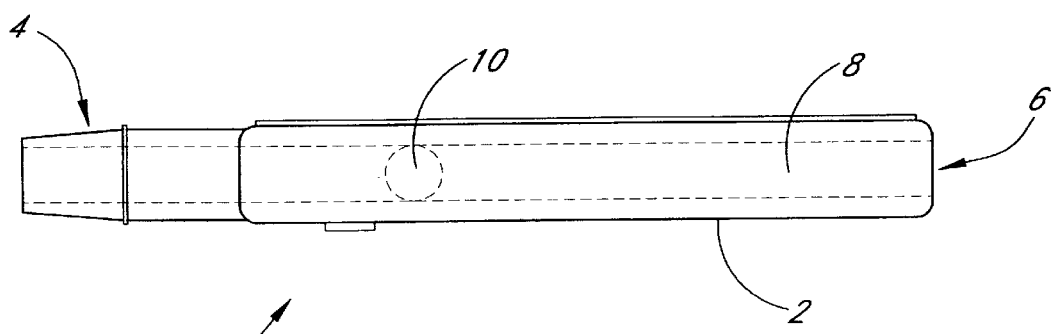
FIG. 7

MANOMETER INFUSION APPARATUS

BACKGROUND OF THE INVENTION

1. Field of the Invention

This invention relates to manometers for fluid infusion and, more particularly, to a manometer for measuring the hydrodynamic pressure of fluids parenterally administered to a patient.

2. Description of the Related Art

Intravenous infusion of fluids into a patient is a routine hospital procedure. Typically, the intravenous infusion apparatus consists of an indwelling catheter that is connected through tubing to a fluid source, such as an elevated glass bottle or plastic bag.

Because of the resistance of the catheter and catheter tubing, and back pressure from the patient, it is sometimes necessary to supply a pressure source such as an electric fluid pump, such as the Harvard pump, or a pump-up pressure cuff. The pressure cuff is placed over the plastic bag containing the fluid and is inflated. In this manner the infusion fluid may be delivered at a particular pressure that is consistent with a desired flow rate for the infusion fluid.

In some situations it is important to provide a carefully controlled flow rate of the infusion fluid. For example, proper administration of some types of medication may require carefully controlled flow rates over long periods of time. Since flow rate is dependent upon the hydrodynamic pressure of the infusion fluid, fluid pressures must be continuously monitored.

In the past, one problem associated with parenteral administration of fluids to a patient has been measuring the hydrodynamic pressure of the fluid being infused into the patient. Typically, it has been assumed that the pressure exerted by the pressure cuff on the fluid-source bag is the same as the pressure exerted on the fluid at its point of infusion into the patient. The level of pressure at the pressure cuff is read directly from a gauge that is associated with the pressure cuff.

However, in practice, the hydrodynamic pressure of the fluid being infused into the patient is not the same as the hydrostatic pressure measured at the pressure cuff. The resistance of the tubing and catheter system and the back pressure of the patient all affect the hydrodynamic pressure of the fluid that is infused into the patient.

To eliminate these inaccuracies, hydrostatic manometers have been developed that may be directly placed in the tubing line and that may be operated to temporarily interrupt the fluid flow so that hydrostatic pressure measurements may be periodically taken. See, for example, U.S. Pat. No. 3,807,389 to Miller et al.

Although these types of in-line manometers provide somewhat accurate pressure readings of the infusion fluid, they do not permit continuous monitoring of hydrodynamic pressures. Since they instead measure hydrostatic pressure, such manometers require periodic interruption of the fluid flow, such as by a stopcock, to obtain a pressure reading. This is inconvenient in some situations and may even be hazardous if the required pressure level drops or rises significantly between readings, resulting in over- or under-infusion.

An in-line, hydrodynamic manometer for measuring infusion pressures is described in U.S. Pat. No. 4,282,881 to Todd et al. This manometer uses a closed pressure-measuring chamber containing a nonexpansible volume of air, which is in communication with a passage through which fluid, whose pressure is to be measured, flows. Several problems exist with this manometer design.

First, there is only one closed pressure-measuring chamber, so the entire apparatus is rather large in order to accommodate a pressure-measuring chamber long enough to measure a given range of pressures. For example, the manometer, as illustrated in FIG. 1 of U.S. Pat. No. 4,282,881, is large enough to require support on a stand.

Second, traditionally there are numerous markings on the housing of the manometer, as shown in FIG. 2 of U.S. Pat. No. 4,282,881, which correspond to various hydrodynamic pressure readings of the fluid flowing through the passage. Again, this results in the need for a relatively long pressure-measuring chamber and thus a relatively large manometer apparatus. Furthermore, because the pressure of intravenous infusions is typically low, from approximately 6 psi at the fluid source to approximately 0.3 psi at the patient's vein, clinical personnel generally do not care about, nor do they need to know, absolute hydrodynamic pressures during intravenous ("IV") infusion of fluid. What is clinically important is whether and when the infusion is in one of three states: 1) flowing relatively freely; 2) obstructed by a distal blockage (i.e., downstream from the manometer, typically at the site of insertion of the IV catheter in the patient's vein); or 3) not flowing at all, either because the IV infusion is turned off or there is a proximal obstruction (i.e., upstream from the manometer, typically close to the fluid source and/or within the associated IV tubing). Thus, the traditional manometer scale with a wide array of absolute pressure markings is, generally, clinically unnecessary.

SUMMARY OF THE INVENTION

From the foregoing, it will be appreciated that what is needed is an in-line manometer that may be used to continuously monitor the hydrodynamic pressure of fluids that are parenterally administered to a patient, and that a) is small and lightweight enough to be suspended conveniently from catheter tubing without need for external support; b) has no moving parts and is disposable; c) has at least one additional closed chamber within the manometer, which is in continuity with a main pressure-measuring chamber, so as to reduce the overall size of the device; and d) has only two or three reference pressure markings on a transparent housing, for indicating the three clinically relevant infusion flow states described above. Such an invention is illustrated and described herein.

The manometer of the present invention provides for continuous, direct, in-line indication of the hydrodynamic pressure or flow of a parenterally administered fluid. The manometer has a passage that permits continuous flow of fluid therethrough. The manometer also consists of a pressure-measuring chamber. One end of the pressure-measuring chamber is in fluid communication with the open passage and the other end of the pressure-measuring chamber communicates with an enclosed air space. The fluid flowing through the passage will enter the pressure chamber and will rise to a level that is dependent upon the pressure of the fluid flowing through the open passage. Markings are placed upon the manometer so that the hydrodynamic pressure of the fluid flowing through the open passage may be easily determined with reference to the level of the fluid in the pressure-measuring chamber, thus providing an indication of the flow through the passage.

In a preferred form of the invention, the flow passage is larger than that which provides the desired flow rate. Instead a restriction having a very small orifice therethrough is positioned in the passage upstream and downstream of the entry to the pressure measuring chamber. The restrictors provide a known pressure drop and a known flow rate. This insures an accurate pressure reading even when the downstream pressure is close to atmospheric, and also provides the desired flow rate.

These and other objects and features of the present invention will become more fully apparent from the following description and appended claims taken in conjunction with the accompanying drawings.

BRIEF DESCRIPTION OF THE DRAWINGS

FIG. 4 is a view of the inlet end of the manometer of FIG. 2.

FIG. 5 is a view of the outlet end of the manometer of FIG. 2.

FIG. 6 is a top view of the manometer of FIG. 2.

FIG. 7 is a bottom view of the manometer of FIG. 2.

DETAILED DESCRIPTION OF THE PREFERRED EMBODIMENT

Figure 1:
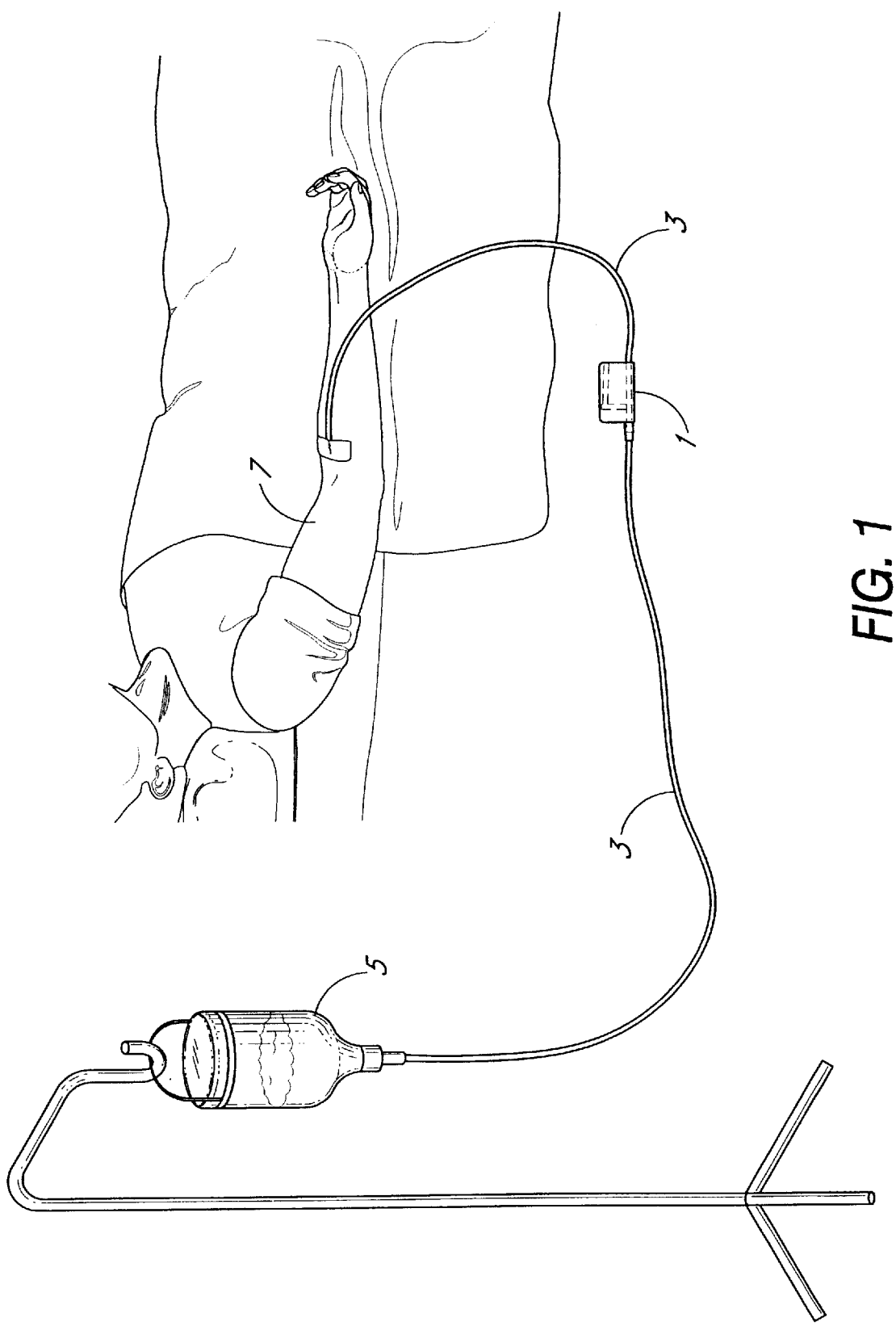
FIG. 1 is an illustration of the manometer apparatus in use with parenteral administration of fluid to a patient.

FIG. 1 illustrates a manometer 1 in use during parenteral fluid administration, e.g., intravenous infusion. Fluid flows, for example, from the patient's parenteral infusion source, such as an intravenous bottle 5 or bag, through intravenous ("IV") tubing 3, and through the manometer 1, to a patient's body 7.

Referring to FIGS. 2 through 7, the manometer 1 includes a housing 2, a fluid inlet 4, and a fluid outlet 6 connected by a passage 8 through which fluid flows to the patient. A tubular pressure-measuring chamber or conduit 10 is in fluid communication with the passage 8 adjacent the outlet 6 and extends generally perpendicular to the passage 8. The distal end 11 of the chamber 10 is closed, and defines a non-expandable volume. Also present is a tubular space-saving chamber 12 or closed end conduit, which is in air communication with the pressure-measuring chamber 10 at the proximal end 13 of the space-saving chamber 12. In the embodiment shown, the chamber 12 extends generally away from the chamber 10, somewhat parallel to the passage 8. This provides a compact arrangement.

Fluid flows from the infusion source 5, into the fluid inlet 4, through the passage 8, and out of the fluid outlet 6, and into the patient's body 7. Since the pressure-measuring chamber 10 is in fluid communication with the passage 8, such that the hydrodynamic pressure of fluid within the passage 8 is translated to the closed pressure-measuring chamber 10.

Markings or indicia 14 are provided on the housing 2 of the manometer 1, which permit the pressure exerted on the fluid flowing through the passage to be read directly from the level of the fluid in the pressure-measuring chamber. In the embodiment shown, several markings 14 are present on the housing 2. These include an "O" marking 20, which indicates that no fluid is flowing through the passage; a rectangular marking 18, which indicates that fluid is flowing through the passage 8; and an "X" marking 16, which indicates that fluid pressure within the pressure-measuring chamber is high, most liklely because there is an obstruction to fluid flow located downstream from the passage 8.

Whereas in previous hydrodynamic manometer systems, the pressure-measuring chamber needed to be relatively long, i.e., large in its long-axis dimension, in order to measure the pressure of fluid flowing into the patient, in the present invention the pressure-measuring chamber 10 can be relatively short because of the presence of a space-saving chamber 12. In certain embodiments, the angle Y (shown in FIG. 2) formed between the long axes of the pressure-measuring chamber 10 and the space-saving chamber 12 is preferably about 90°, such that the chamber 12 extends roughly parallel to the passage 8, thereby minimizing the size of the housing 2.

One function of the space-saving chamber is to reduce the length of the long axis of the pressure measuring chamber 10. The space-saving chamber 12 accomplishes this goal by allowing air communication with the pressure-measuring chamber 10, such that the combined volume of air within the pressure-measuring chamber 10 and the space-saving chamber 12 is sufficient, through compression and expansion, to permit accurate detection of the flow states within the passage 8. That is, the length of the chamber 10 is not by itself sufficient to trap a volume of air to adequately indicate pressure changes.

There are three clinically important flow states that are detected by the present system: 1) fluid in the passage 8 is flowing relatively freely; 2) flow through the passage 8 is obstructed by a distal blockage (i.e., downstream from the manometer, typically at the site of insertion of the IV catheter in the patient's vein); or 3) fluid is not flowing through the passage 8 at all, or is flowing at insubstantial flow rates, either because the IV infusion is turned off or there is a proximal obstruction (i.e., upstream from the manometer, typically close to the fluid source and/or within the associated IV tubing).

Detection of the flow states within the passage 8 is dependent upon the pressure of fluid that is within the passage 8. As fluid pressure within the passage rises, a column of fluid rises within the pressure-measuring chamber 10 to a level which is dependent upon the pressure of the fluid flowing through the passage 8. The flow state of fluid within the passage 8 can thence be determined by an examiner, typically a nurse or other caregiver, by ascertaining where the leading edge, or top, of the fluid column within the pressure-measuring chamber 10 is in comparison to certain reference markings that are associated with, and are present alongside, the pressure-measuring chamber 10.

As seen from the drawings, the housing 2 has a thin, flat, rectangular configuration. It is preferably made of suitable transparent plastic that is relatively inexpensive, such that it is quite practical as a disposable item. The manometer 1 is small and lightweight and hence easily attached to infusion tubing 3 without any separate support, strain on the tubing 3, or inconvenience to the patient. In a prototype form of the manometer 1, the housing 2 is only about 3 centimeters long and about 2 centimeters wide. This places the longer centerline of the housing 2 only about 1 centimeter from the tubing 3 of FIG. 1, thus minimizing torque load on the tubing 3. In thickness, the housing 2 is about the same as the outside diameter of the tubing 3 connected to the housing 2, as seen from FIGS. 4, 6 and 7. This is about 0.4 centimeters.

Through the use of the space-saving chamber 12, the pressure-measuring chamber 10 can be significantly diminished in length along its long axis, relative to devices used in the prior art. In certain embodiments, the pressure-measuring chamber 10 is less than 3.0 centimeters in length along its long axis, as measured from the passage 8 to the distal end 11 of the pressure-measuring chamber 10. In these embodiments, the pressure-measuring chamber 10 is less than 2 centimeters in length, the prototype being only about 1.5 centimeters along its long axis. In the arrangement shown, the space-saving chamber 12 is a little less than twice as long as the pressure-measuring chamber 10.

Figure 8:
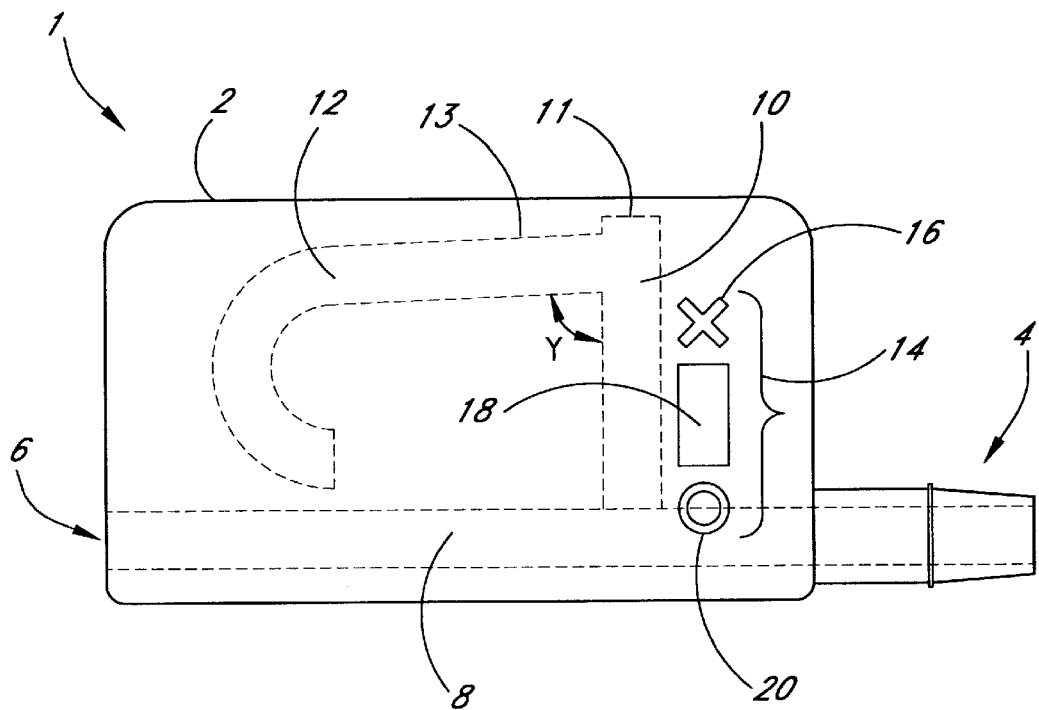
FIG. 8 is a front elevational view of another embodiment of the manometer of the invention, illustrating a curved space-saving chamber.

As illustrated in FIG. 8, in another embodiment, the space-saving chamber 12 is curved, resembling a partial arc or coil, which is in air communication with the pressure-measuring chamber 10 at the proximal end 13 of the space-saving chamber 12. As seen, the end 13 extends away from the chamber 12 at an angle Y of about 90°, and its distal end curves toward the passage 8 and then back upon itself towards the chamber 10, thus making about 180° turn. This arc or coil configuration design is space-saving, as it enables the reduction of the overall size of the housing 2, while providing the necessary length for the chambers.

Figure 2:
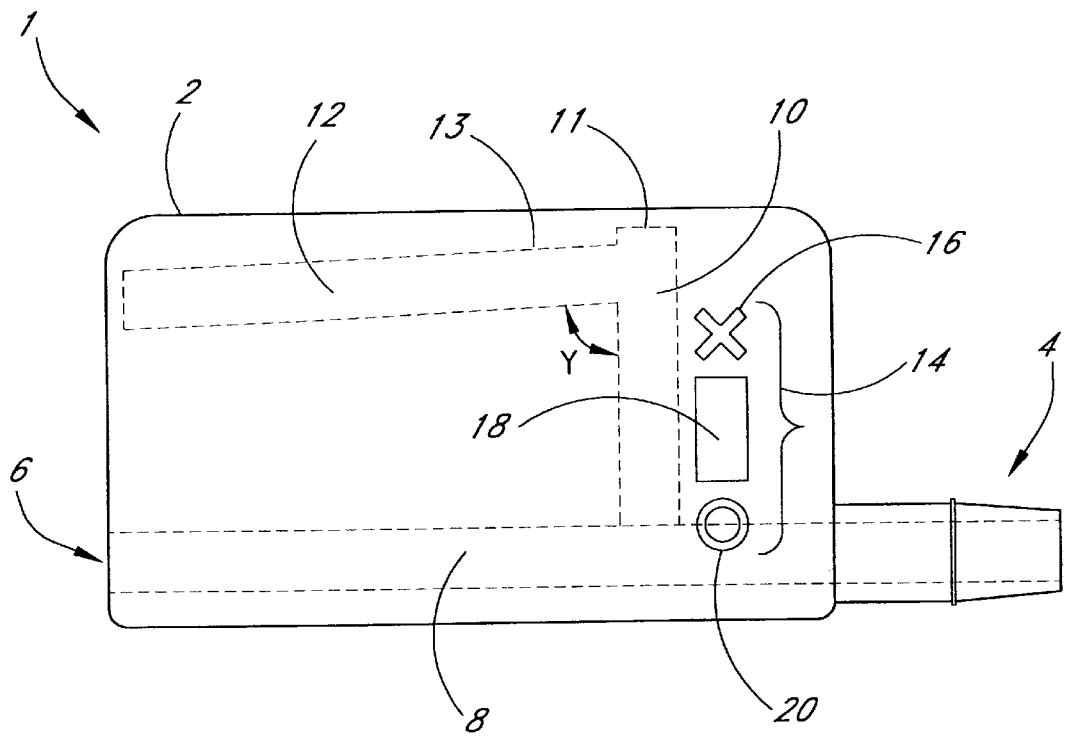
FIG. 2 is a front elevational view of the manometer of FIG. 1.
Figure 3:
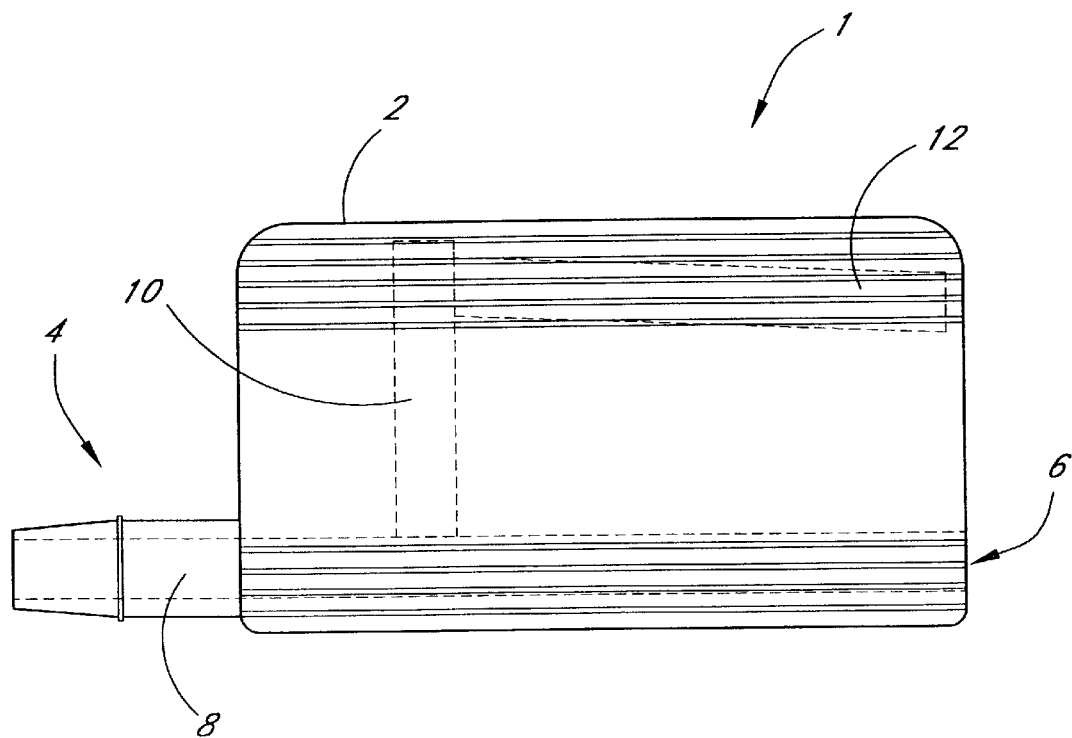
FIG. 3 is a rear view of the manometer shown in FIG. 2.

Also illustrated in FIG. 8 are several markings 14 on the housing 2 as in FIG. 2. These markings 14 consist of an "O" marking 20, which indicates that no fluid is flowing through the passage; a rectangular marking 18, which indicates that fluid is flowing through the passage 8; and an "X" marking 16, which indicates that there is an obstruction to fluid flow located downstream from the passage 8.

While the above arrangements will function as described, greater accuracy of flow rate and pressure indications may be desirable, particularly with low flow rates. For example, the difference in the pressure at the entrance to the space 10 and in the patient's vein is dependent on the resistance to flow in the tubing between the space 10 and the patient. While this is a fixed resistance for the tubing selected, tubing of various sizes and various lengths and materials may be utilized. Also, while venous pressure is quite low, it does vary. Hence, both of these variables would affect the level of the liquid rising into the space 10.

Figure 9:
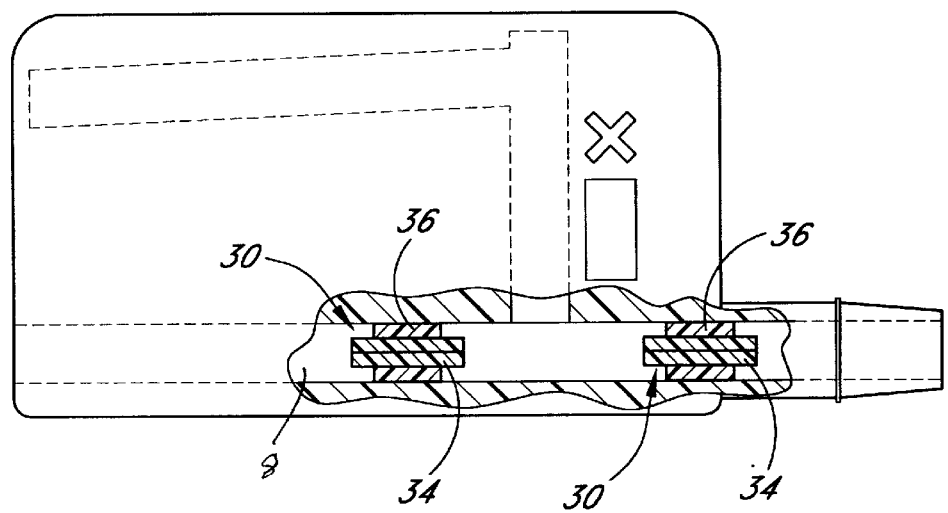
FIG. 9 illustrates a modification of the manometers of FIGS. 1 and 8.

With low flow rates, it is necessary to carefully calculate the resistance to flow in the passage 8. Rather than calculating the characteristics of the plastic manometer body to obtain the desired flow rate, FIG. 9 illustrates a modification of the above arrangements that provides the desired accuracy regarding flow rates and greater accuracy on pressure indications by the manometer. As shown, a restrictor 30 is positioned in the passage 8 upstream from the entry to the space 10, and a similar restrictor 32 is positioned in the passage 8 downstream of the entry to the space 10. Each of these restrictors comprises a glass tube 34 and a surrounding annular seal 36, preferably made of silicon rubber. The glass tube 34 has a very small inner diameter, such as in the range of 0.001 to 0.004 inches. In a production version of the device, the diameter is in the range of 0.001 to 0.002 inches. The OD of that device is approximately 0.050 inches. The length of the glass tube is selected to provide a desired pressure drop across each of the restrictors and a desired flow rate. With the diameter of the passage 8 being so large relative to the orifice in the restrictor, the resistance to low downstream from the restrictor 32 is very low, essentially atmospheric.

In a production version of the device, the length of the restrictors was selected to be about 0.3 inches. Assuming an input pressure to the manometer is about 6 psi, the restrictor 30 was selected to create a pressure drop of about 3 psi. That pressure applied to the space 10 will result in the fluid moving into the message 10 maintaining a level in the desired range between the O and the X indicators. A similar pressure drop of about 3 psi is created by the downstream restrictor 32, and the combination of the two restrictors will create the desired flow rate for the device. Because the pressure downstream of the restrictor 32 is essentially atmospheric, and because of the size difference between the orifice in the restrictor 32 and the diameter of the passage 8, the restrictor 32 is needed in order to obtain a proper reading on the manometer when the flow is at a satisfactory rate. That is, if there were no downstream restrictor, the indicator would be zero. Similarly, if there is a downstream restrictor 32 but there is no upstream restrictor 30, the pressure indicated on the manometer would be closer to the pressure at the fluid source. Thus, there would be little or no difference between a normal flow and a blockage of flow downstream of the downstream restrictor.

It should be recognized that the specifics of the pressure drops and flow rates would need to be determined for each situation.

Although the present invention has been described in terms of certain preferred embodiments, other embodiments of this invention will become apparent to those of skill in the art in view of the disclosure herein. Accordingly the scope of the present invention is not intended to be limited by the foregoing, but rather by reference to the attached claims.

What is claimed is:

1. A manometer for measuring the hydrodynamic pressure of fluids parenterally administered to a patient, said manometer comprising:
 a housing having a fluid inlet and a fluid outlet;
 a continuously open passage formed in said housing, said passage accommodating continuous flow of fluid therethrough from said fluid inlet to said fluid outlet;
 a pressure-measuring chamber formed in said housing, one end of said pressure-measuring chamber being in fluid communication with said passage, said pressure-measuring chamber having at the other end thereof a normally closed air space that defines a non-expansible volume;
 a space-saving chamber formed in said housing, one end of said space-saving chamber being in air communication with said pressure-measuring chamber, said space-saving chamber having at the other end thereof a normally closed air space that defines a non-expansible volume; and
 indicia associated with said pressure-measuring chamber, for indicating the pressure of the fluid flowing through said passage.

2. The manometer of claim 1, wherein said pressure-measuring chamber extends generally perpendicularly to said passage, and the space-saving chamber extends generally perpendicular to said pressure-measuring chamber.

3. The manometer of claim 1, wherein said pressure-measuring chamber is less than 3.0 centimeters in length.

4. The manometer of claim 1, wherein said pressure-measuring chamber is less than 2.0 centimeters in length.

5. The manometer of claim 1, wherein said pressure-measuring chamber is about 1.6 centimeters or less in length.

6. The manometer of claim 1, wherein a distal end of said space-saving chamber curves back toward said pressure-measuring chamber.

7. The manometer of claim 1, wherein said indicia comprises:

a marking indicating that substantially no fluid is flowing into said passage; and a marking indicating that there is an obstruction to fluid flow, said obstruction being located downstream from said passage.

8. The manometer of claim 1, wherein said indicia includes a marking indicating that fluid is flowing through said passage.

9. A manometer for measuring the hydrodynamic pressure of fluids parenterally administered to a patient, said manometer comprising:

a housing having a fluid inlet and a fluid outlet;

a continuously open passage formed in said housing, said passage accommodating continuous flow of fluid therethrough from said fluid inlet means to said fluid outlet means;

a pressure-measuring chamber formed in said housing, one end of said measuring chamber being in fluid communication with said passage, said pressure-measuring chamber having at the other end thereof a normally closed air space that defines a non-expansible volume;

means for minimizing the length of said pressure-measuring chamber; and reference markings, associated with said pressure-measuring chamber, for indicating the pressure of the fluid flowing through said passage;

wherein the means for minimizing the length of said pressure-measuring chamber is a space-saving chamber formed in said housing, one end of said space-saving chamber being in air communication with said pressure-measuring chamber, said space-saving chamber having at the other end thereof a normally closed air space that defines a non-expansible volume.

10. A manometer for measuring the hydrodynamic pressure of fluids parenterally administered to a patient, said manometer comprising:

a housing having a fluid inlet and a fluid outlet;

a continuously open passage formed in said housing, said passage accommodating continuous flow of fluid therethrough from said fluid inlet means to said fluid outlet means;

a pressure-measuring chamber formed in said housing, one end of said measuring chamber being in fluid communication with said passage, said pressure-measuring chamber having at the other end thereof a normally closed air space that defines a non-expansible volume;

means for minimizing the length of said pressure-measuring chamber; and reference markings, associated with said pressure-measuring chamber, for indicating the pressure of the fluid flowing through said passage;

wherein the means for minimizing the length of said pressure-measuring chamber is a space-saving chamber formed in said housing, one end of said space-saving chamber being in air communication with said pressure-measuring chamber, said space-saving chamber having at the other end thereof a normally closed air space that defines a non-expansible volume;

wherein said housing has a thin, flat, generally rectangular shape, said pressure-measuring chamber extends away from the passage, and said space-saving passage extends substantially no further away from said passage than said pressure measuring chamber so as to provide a compact arrangement.

11. A manometer for measuring the hydrodynamic pressure of fluids parenterally administered to a patient, said manometer comprising:

a housing having a fluid inlet and a fluid outlet;

a continuously open passage formed in said housing, said passage accommodating continuous flow of fluid therethrough from said fluid inlet means to said fluid outlet means;

a pressure-measuring chamber formed in said housing, one end of said measuring chamber being in fluid communication with said passage, said pressure-measuring chamber having at the other end thereof a normally closed air space that defines a non-expansible volume;

means for minimizing the length of said pressure-measuring chamber; and reference markings, associated with said pressure-measuring chamber, for indicating the pressure of the fluid flowing through said passage;

wherein the means for minimizing the length of said pressure-measuring chamber is a space-saving chamber formed in said housing, one end of said space-saving chamber being in air communication with said pressure-measuring chamber, said space-saving chamber having at the other end thereof a normally closed air space that defines a non-expansible volume;

wherein said housing has a thin, flat, generally rectangular shape, said pressure-measuring chamber extends away from the passage, and said space-saving passage extends substantially no further away from said passage than said pressure measuring chamber so as to provide a compact arrangement;

wherein said housing is formed of transparent, rigid plastic to permit fluid in said pressure measuring chamber to be seen.

12. A manometer for measuring the hydrodynamic pressure of fluids being administered to a patient, said manometer comprising:

a housing having a fluid inlet and a fluid outlet;

a continuously open passage formed in the housing extending between the inlet and the outlet;

a chamber formed in the housing with one end open to the passage and the other end being closed to define an air space; and a restrictor in said passage upstream from said chamber, and a restrictor in said passage downstream of said space, said restrictors each having an orifice that permits flow through the passage but which creates a pressure drop across each restrictor and hence creates a desired pressure between the restrictors which is applied to said chamber, and provides a desired flow rate through the passage;

wherein each restrictor comprises a tube having a small inner diameter forming said orifice, and a ring-shaped seal surrounding the tube and extending between the tube and the surrounding passage so that fluid flow through the orifices in the restrictors is the only flow through the restrictors.

13. A manometer for measuring the hydrodynamic pressure of fluids being administered to a patient, said manometer comprising:

a housing having a fluid inlet and a fluid outlet;

a continuously open passage formed in the housing extending between the inlet and the outlet;

a chamber formed in the housing with one end open to the passage and the other end being closed to define an air space; and a restrictor in said passage upstream from said chamber, and a restrictor in said passage downstream of said space, said restrictors each having an orifice that permits flow through the passage but which creates a pressure drop across each restrictor and hence creates a desired pressure between the restrictors which is applied to said chamber, and provides a desired flow rate through the passage;

wherein said upstream restrictor reduces the pressure to half that of the pressure applied to the upstream side of the upstream restrictor, and the diameter of the passage downstream of the downstream restrictor is substantially larger than the orifice through the downstream restrictor such that the pressure downstream of the downstream restrictor is essentially atmospheric.

* * * * *